US008864820B2

(12) United States Patent
Foreman et al.

(10) Patent No.: US 8,864,820 B2
(45) Date of Patent: Oct. 21, 2014

(54) SELECTIVE COATING OF AN IMPLANTABLE MEDICAL DEVICE

(71) Applicant: Abbott Cardiovascular Systems Inc., Santa Clara, CA (US)

(72) Inventors: Philip Foreman, San Jose, CA (US); Charles W. Snyder, San Francisco, CA (US); Gregg Teaby, Sunnyvale, CA (US); Eric Penn, Morgan Hill, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/969,476

(22) Filed: Aug. 16, 2013

(65) Prior Publication Data

US 2014/0004312 A1    Jan. 2, 2014

Related U.S. Application Data

(62) Division of application No. 11/853,734, filed on Sep. 11, 2007, which is a division of application No. 10/932,364, filed on Aug. 31, 2004, now abandoned.

(51) Int. Cl.
| | |
|---|---|
| A61F 2/06 | (2013.01) |
| A61L 31/08 | (2006.01) |
| A61L 31/16 | (2006.01) |
| A61L 31/14 | (2006.01) |
| A61L 31/10 | (2006.01) |
| A61F 2/82 | (2013.01) |

(52) U.S. Cl.
CPC ............. *A61L 31/08* (2013.01); *A61L 2420/02* (2013.01); *A61L 31/16* (2013.01); *A61L 31/14* (2013.01); *A61L 31/10* (2013.01); *A61F 2/82* (2013.01)
USPC ........................................................ 623/1.46

(58) Field of Classification Search
CPC ........................................................ A61F 2/82
USPC ........................................................ 623/1.46
See application file for complete search history.

(56) References Cited

U.S. PATENT DOCUMENTS

| | | | | |
|---|---|---|---|---|
| 8,147,898 B2 * | 4/2012 | Coates et al. | ................ | 427/2.24 |
| 2003/0139801 A1 * | 7/2003 | Sirhan et al. | ................ | 623/1.15 |

* cited by examiner

*Primary Examiner* — David Isabella
*Assistant Examiner* — Jacqueline Woznicki
(74) *Attorney, Agent, or Firm* — Squire Patton Boggs (US) LLP

(57) ABSTRACT

A coating and a method of coating an implantable medical device, such as a stent, is disclosed. The coating compensates for regions of higher stress and resulting strain due to the geometry of the device. Certain embodiments may include a nonuniform coating on the device in which a strain on the nonuniform coating is less than a strain on a uniform coating when the device is placed under an applied stress during use. Other embodiments may include a coating with a greater resistance to strain on higher strain regions of the device.

12 Claims, 8 Drawing Sheets

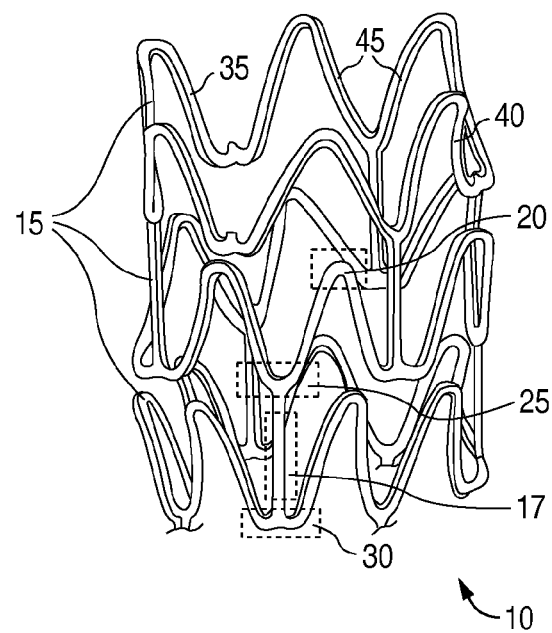
FIG. 1A
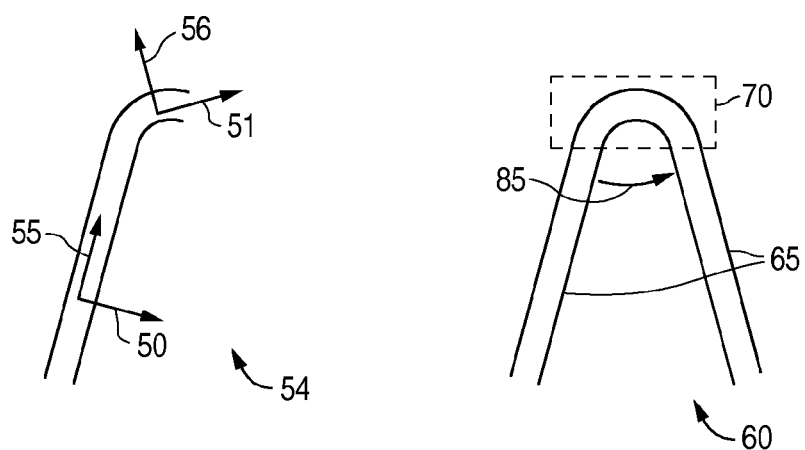
FIG. 1B
FIG. 2A
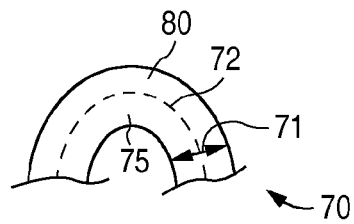
FIG. 2C

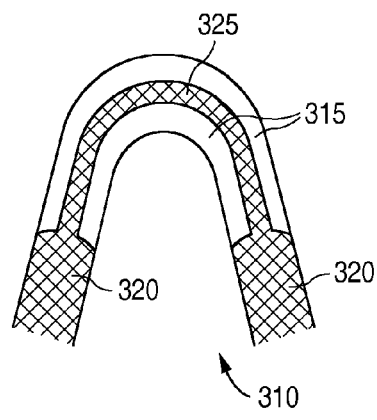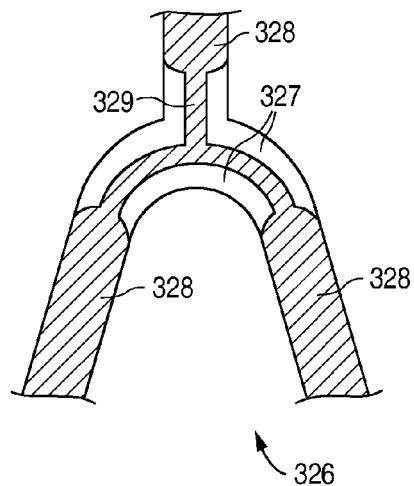
FIG. 9A  FIG. 9B
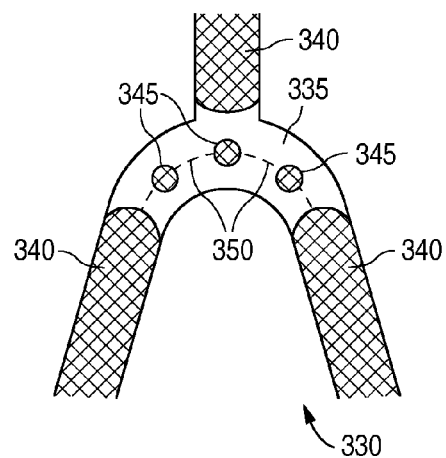
FIG. 10

SELECTIVE COATING OF AN IMPLANTABLE MEDICAL DEVICE

CROSS-REFERENCE TO RELATED APPLICATIONS

This application is a divisional of application Ser. No. 11/853,734, filed Sep. 11, 2007, which is a divisional of application Ser. No. 10/932,364, filed Aug. 31, 2004, both of which are incorporated herein by reference.

BACKGROUND OF THE INVENTION

1. Field of the Invention

The invention relates to drug delivery implantable medical devices, one example of which is a stent. More particularly, the invention relates to selectively coating a device to accommodate differences in strain experienced by different portions of a device during use.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to remodel the vessel wall. The balloon is then deflated to a smaller profile to allow the catheter to be withdrawn from the patient's vasculature.

A problem associated with the above procedure includes formation of intimal flaps or torn arterial linings, which can collapse and occlude the conduit after the balloon is deflated. Vasospasms and recoil of the vessel wall also threaten vessel closure. Moreover, thrombosis and restenosis of the artery may develop over several months after the procedure, which may necessitate another angioplasty procedure or a surgical by-pass operation. To reduce the partial or total occlusion of the artery by the collapse of arterial lining and to reduce the chance of the development of thrombosis and restenosis a stent is implanted in the lumen to maintain the vascular patency.

Stents act as scaffoldings, functioning to physically hold open and, if desired, to expand the wall of the passageway. Typically, stents are capable of being compressed or crimped onto a catheter so that they can be delivered to and deployed at a treatment site. Delivery includes insertion through small lumens via a catheter and transporting the stent to the treatment site. Deployment includes expanding the stent to a larger diameter once it is at the desired location. Mechanical intervention via stents has reduced the rate of restenosis as compared to balloon angioplasty. Yet, restenosis remains a significant problem. When restenosis does occur in the stented segment, its treatment can be challenging, as clinical options are more limited as compared to lesions that were treated solely with a balloon.

Stents are used not only for mechanical intervention but also as vehicles for providing biological therapy. Biological therapy can be achieved by medicating the stents. Medicated stents provide for the local administration of a therapeutic substance at the diseased site. In order to provide an efficacious concentration to the treated site, systemic administration of such medication often produces adverse or even toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

To fabricate a conventional coating, a polymer, or a blend of polymers, can be applied on the stent using techniques known to those having ordinary skill in the art. A composition for applying to a stent may include a solvent, a polymer dissolved in the solvent, and an active agent dispersed in the blend. The composition may be applied to the stent by immersing the stent in the composition or by spraying the composition onto the stent. The solvent is allowed to evaporate, leaving on the stent strut surfaces a coating of the polymer and the active agent impregnated in the polymer. Selective coating of an implantable medical device, such as a stent, is described herein.

A potential shortcoming of the foregoing method of medicating stents is that a polymeric drug coating disposed directly on the surface of the stent may not attach well to the surface during crimping, deployment, or implantation of the stent as well as while the stent is in a patient. Some polymers applied on stents, for example, are relatively brittle at biological conditions (i.e., are capable of relatively small percent elongation before fracture). During deployment, the polymeric stent coating can be exposed to stress caused by the radial expansion of the stent body. In addition, a polymeric stent coating may be exposed to stress when it is mounted on a catheter from crimping or compression of the stent. These stresses can cause the coating to tear or fracture. Failure of the mechanical integrity of the stent while the stent is localized in a patient can lead to a serious risk of embolization caused by a piece of the polymeric coating breaking off from the stent. Polymeric stent coatings having a high drug loading are especially vulnerable to fracture during and after deployment. Active agents tend to increase the crystallinity of a coating. As a result, elasticity of the coating may be decreased which makes the coating more susceptible to failure when subjected to high stress.

It is therefore desirable to improve the adhesion or retention of the polymeric coating to the surface of a stent. It is also desirable to be able to increase the quantity of the therapeutic substance carried by the polymeric layer without perturbing the mechanical properties of the coating, such as inadequate coating adhesion. It is additionally desirable to provide an improved polymeric coating that is capable of delivery and expansion with a stent without any or significant detachment from the surface of the stent. The present invention meets the foregoing as well as other needs.

SUMMARY

The present invention is directed to implantable medical devices, such as stents that include a first section that has higher strain than a second section when the device is placed under an applied stress during use. Certain embodiments may include a nonuniform coating on the device in which a strain on the nonuniform coating is less than a strain on a uniform coating when the device is placed under the applied stress during use. A further aspect of the invention is directed to implantable medical devices and methods of manufacturing such devices that include a first coating on the first section of the device that has greater resistance to strain than a coating on the second section.

The present invention includes embodiments of a stent with a structural element having a variable strain profile under applied stress along a length of the element and a coating on the stent. The coating may be selectively positioned on the stent or modified in character or type so as to accommodate the variable strain profile along the length of the element so as to prevent the coating from fracturing, pealing or delaminating off of the stent or reduce fracturing, pealing or delaminating of the coating off of the stent as compared to a coating on a stent that has not been selectively positioned or modified.

BRIEF DESCRIPTION OF THE FIGURES

FIG. 1A depicts a stent.
FIG. 1B depicts a portion of a strut.
FIGS. 2A-C, 3A-B, and 4A-B depict portions of a stent.
FIGS. 8A-C, 9A-B, 10, 11A-C, and 12 depict nonuniform coating embodiments on surfaces of a stent.

DETAILED DESCRIPTION

Figure 2B:
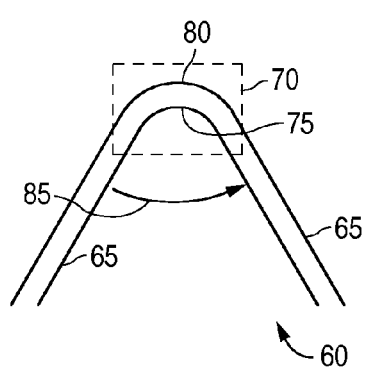

For the purposes of the present invention, the following terms and definitions apply:

The "glass transition temperature," $T_g$, is the temperature at which the amorphous domains of a polymer change from a brittle vitreous state to a solid deformable state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in volume and/or length). In addition, compressive stress is a normal component of stress applied to materials resulting in their compaction (decrease in volume and/or length). Stress may result in deformation of a material, which refers to change in length and/or volume. "Expansion" or "compression" may be defined as the increase or decrease in length and/or volume of a sample of material when the sample is subjected to stress. "Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

Furthermore, a property of a material that quantifies a degree of deformation with applied stress is the modulus. "Modulus" may be defined as the ratio of a component of stress or force per unit area applied to a material divided by the strain along an axis of applied force that results from the applied force. For example, a material has both a tensile and a compressive modulus.

The tensile stress on a material may be increased until it reaches an "ultimate tensile strength" which refers to the maximum tensile stress which a material will withstand prior to fracture. The ultimate tensile strength is calculated from the maximum load applied during a test divided by the original cross-sectional area. Similarly, "ultimate compressive strength" is the capacity of a material to withstand axially directed pushing forces. When the limit of compressive strength is reached, a material is crushed.

The term "elastic deformation" refers to deformation of an object in which the applied stress is small enough so that the object retains its original dimensions or essentially its original dimensions once the stress is released. However, an elastically deformed polymer material may be prevented from returning to an undeformed state if the material is below the $T_g$ of the polymer. Below $T_g$, energy barriers may inhibit or prevent molecular movement that allows deformation or bulk relaxation. "Elastic limit" refers to the maximum stress that a material will withstand without permanent deformation. The term "plastic deformation" refers to permanent deformation that occurs in a material under stress after elastic limits have been exceeded.

"Elasticity" refers to the ability of a material to deform without failure when subjected to an applied stress. For example, as a temperature of a polymer is increased from below to above its $T_g$, its elasticity increases. The elasticity of the polymer increases from a relatively inelastic state to more elastic states. Polymers that have a relatively high elasticity are flexible and have a relatively low modulus. Conversely, polymers with relatively low elasticity tend to be brittle and have a relatively high modulus. Elasticity is, accordingly, a relative term. Between two polymers, whichever one has the lower modulus has the higher elasticity.

"Neutral axis" refers to a line or plane in a member subjected to a stress at which the strain is zero. For example, a beam in flexure due to stress (e.g., at a top face) has tension on one side (e.g., the bottom face) and compression on the other (e.g., the top face). The neutral axis lies between the two sides at a location or locations of zero strain. The neutral axis may correspond to a surface. If the beam is symmetric (in both geometry and materials) the neutral axis is at the geometric centroid (center of mass) of the beam. The strain increases in either direction away from the neutral axis.

"Nonuniform" is defined as, unless otherwise specifically indicated, one or a combination of the following embodiments, unless specifically excluded: (1) no coating or coating free in some portions of the device; (2) use of different materials (e.g., polymers) or combination of materials; (3) coating having no drug content or different amount of drug at selected portions of the device; (4) coating having different types of drug at selected portions of the device; (5) coating having different thickness at selected portions of the device; (6) coating material (e.g., polymer) having different characteristics (such as elasticity) at different areas of the device; (7) use of different coating additives or plasticizers at selected portions of the device, and (8) different quantity of coating material at selected areas of the device.

"Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure.

Embodiments of devices described herein relate to implantable medical devices that include an underlying scaffolding or substrate with a coating such as a polymer-based coating. The polymer-based coating may contain, for example, an active agent or drug for local administration at a diseased site. The active agent can be any substance capable of exerting a therapeutic or prophylactic effect. The underlying substrate that is coated can be polymeric, metallic, ceramic, or made from any suitable material. Implantable medical device is intended to include self-expandable stents, balloon-expandable stents, stent-grafts, grafts (e.g., aortic grafts), artificial heart valves, cerebrospinal fluid shunts, pacemaker electrodes, and endocardial leads (e.g., FINE-LINE and ENDOTAK, available from Guidant Corporation, Santa Clara, Calif.). The underlying structure or substrate of the device can be of virtually any design.

To fabricate the coating, the polymer, or a blend of polymers, can be applied on the stent using common techniques known to those having ordinary skill in the art. For example, the polymer can be applied to the stent by dissolving the polymer in a coating solvent, or a mixture of solvents, and applying the resulting solution on the stent by spraying, "ink-jet-type" deposition methods, brushing, plasma deposition, and the like.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an implantable medical device, include, but are not limited to, poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(D-lactic acid), poly(D-lactide), poly(caprolactone), poly(L-lactide-co-ε-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating or coating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

In addition, polymers containing moieties derived from poly(lactic acid) can be also used in addition to or instead of, poly(lactic acid), for fabricating and coating devices. Polymers based on poly(lactic acid) include derivatives of poly (lactic acid), for example, hydrolyzed or carboxylated poly (lactic acid), or a blend thereof Using the hydrolyzed or carboxylated poly(lactic acid) is expected to result in the increased rate of degradation of the coating. Another type of polymer based on poly(lactic acid) that can be used for fabricating and coating implantable medical devices includes graft copolymers, and block copolymers, such as AB block-copolymers ("diblock-copolymers") or ABA block-copolymers ("triblock-copolymers"), or mixtures thereof.

Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof Other therapeutic substances or agents may include rapamycin and structural derivatives or functional analogs thereof, such as 40-O-(2-hydroxy)ethyl-rapamycin (known by the trade name of EVEROLIMUS), 40-O-(3-hydroxy)propyl-rapamycin, 40-O-[2-(2-hydroxy)ethoxy]ethyl-rapamycin, methyl rapamycin, and 40-O-tetrazole-rapamycin.

A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

Implantable medical devices are typically subjected to stress during use, both before and during treatment. "Use" includes manufacturing, assembling (e.g., crimping a stent on balloon), delivery of a stent through a bodily lumen to a treatment site, and deployment of a stent at a treatment site. Both the underlying scaffolding or substrate and the coating experience stress that result in strain in the substrate and coating. Generally, the stress and the resulting strain throughout the structure of a stent are not uniform. As indicated above, localized portions of the stent's structure undergo substantial deformation. It follows that the degree of stress and strain experienced by various portions of the device may be across a broad spectrum. Some portions may experience no or substantially no stress and strain, while other portions may experience relatively high stress and strain. Additionally, some regions may experience tensile stress and strain, while others may experience compressive stress and strain. In general, it is advantageous for regions of a stent that experience relatively high stress and strain during use to be more elastic or flexible than regions that experience relatively low stress and strain.

It is important for a device to be mechanically stable throughout the range of stress and strain experienced throughout the manufacturing, assembly, and particularly during radial adjustment for a stent. Mechanical instability may include failure of the substrate or coating that may include tearing or fracture and/or detachment of the coating from the surface of the device.

Furthermore, polymer-based coatings may be particularly vulnerable to mechanical instability during use of an implantable medical device. Polymers, in general, and many polymers used in coatings for devices tend to have a relatively high degree of inelasticity, and, hence have relatively low strength compared to a metal. Polymers can have an ultimate strain as low as 5% of plastic strain. Therefore, polymer-based coatings are highly susceptible to tearing or fracture and/or detachment at regions subjected to relatively high stress and strain of an implantable medical device, particularly for polymers having a $T_g$ above the body temperature. The temperature of the polymer in the coating never reaches the $T_g$ of the polymer during treatment. As a result, the polymer does not remain sufficiently elastic.

Embodiments described herein may be illustrated by a stent. FIG. 1A depicts an example of a three-dimensional view of a stent 10. The stent may have a pattern that includes a number of interconnecting elements or struts 15. The embodiments disclosed herein are not limited to stents or to the stent pattern illustrated in FIG. 1A. The embodiments are easily applicable to other patterns and other devices. The variations in the structure of patterns are virtually unlimited. As shown in FIG. 1A the geometry or shape of stents vary throughout its structure. A pattern may include portions of struts that are straight or relatively straight, an example being a section 17. In addition, patterns may include struts that include curved or bent portions as in a section 20. Patterns may also include intersections of struts with curved or bent portions as in sections 25 and 30.

Additionally, a surface of an implantable medical device may also be characterized by the relative location of the surface with respect to a bodily lumen. The device may include luminal surfaces or outer portions, abluminal surfaces or inner portions, and surfaces between the luminal and abluminal surfaces. For example, struts 15 of stent 10 include abluminal surfaces or faces 35, luminal surfaces or faces 40, and side-wall surfaces or faces 45. A strut may also be described by axes, a latitudinal axis and a longitudinal axis. FIG. 1B depicts a portion 54 of a strut depicting a latitudinal axis 50 and a longitudinal axis 55 along a straight section of portion 54. A longitudinal axis 51 on a curved section of a strut may be defined as a tangent to a curvature at a location on the curved section. A corresponding latitudinal axis 56 is perpendicular to longitudinal axis 51. In other embodiments, the latitudinal cross-section may include any number of faces or be a curved surface. The pattern that makes up the stent allows the stent to be radially expandable and longitudinally flexible. Longitudinal flexibility facilitates delivery of the stent and radial rigidity is needed to hold open a body lumen. The pattern should be designed to maintain the longitudinal flexibility and radial rigidity required of the stent.

As indicated above, the stress and strain experienced by an implantable medial device during use is not uniform throughout the substrate and the coating. For instance, the stress and strain experienced by a stent in a radially expanded state are different in various portions of the stent. Some portions of a stent pattern may have no or relatively no strain, while others may have relatively high strain. Straight or substantially straight sections of struts such as section 17 of stent 10 in FIG. 1A experience no or relatively no strain. However, sections 20, 25, and 30 experience relatively high strain when the stent is expanded or crimped.

FIGS. 2A-C, 3A-B, and 4A-B depict partial planar side views of luminal or abluminal surfaces from a stent. The figures illustrate the nonuniformity of stress and strain in an implantable medical device. FIG. 2A depicts a partial planar side view of a portion 60 from a stent in an unexpanded state that includes straight sections 65 and a curved section 70 with an angle 85. When a stent undergoes radial expansion, portions of struts bend resulting in an increase of angle 85 between straight sections 65, as shown in FIG. 2B. FIGS. 2A and 2B depict portion 60 in a plane of bending. The bending of portion 60 causes no or substantially no strain in straight sections 65. However, the bending of section 60 causes relatively high stress and strain in most of curved section 70. A concave portion 75 of curved section 70 experiences relatively high tensile stress and strain and a convex portion 80 of curved section 70 experiences relatively high compressive strain. When a stent is crimped, angle 85 decreases and concave portion 75 experiences relatively high compressive strain and convex portion 80 experiences relatively high tensile strain. FIG. 2C depicts an expanded view of curved section 70 with a neutral axis 72 indicated. The strain along the neutral axis is zero. In the stent, the neutral axis corresponds to a surface of zero strain. For a strut that is symmetric along its longitudinal and latitudinal axis, the neutral axis may be a geometric centroid perpendicular to a plane of bending (i.e., perpendicular to the plane of the sheet of paper). In the case of portion 70 in FIG. 2C, neutral axis 72 runs along the midpoint or center of a latitudinal width 71 of curved section 70. Therefore, in a small, narrow region of curved section 70 along neutral axis 72, there is zero or relatively low strain.

Figure 3A:
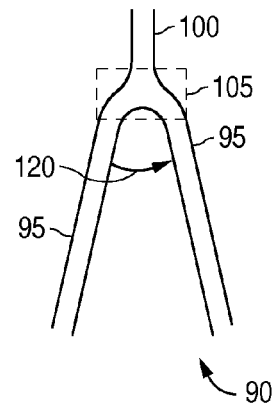
Figure 3B:
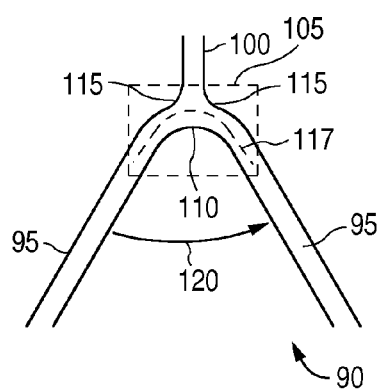

FIG. 3A depicts a partial planar side view of a portion 90 from a stent in an unexpanded state that includes a curved section 105, straight sections 95 at an angle 120, and straight section 100. As shown in FIG. 3B, radial expansion of the stent increases angle 120. The stress and strain in straight sections 95 and 100 is relatively small. Section 105 experiences relatively high tensile stress and strain at concave portion 110 and relatively high compressive stress and strain at portion 115. A neutral axis 117 is a surface of zero strain that is the boundary between portion 110 and portion 115.

Figure 4A:
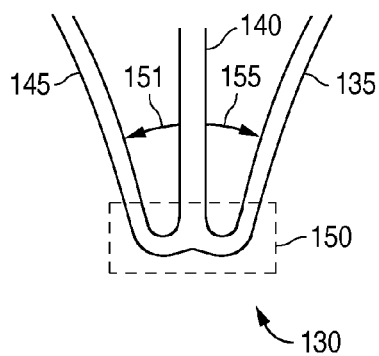
Figure 4B:
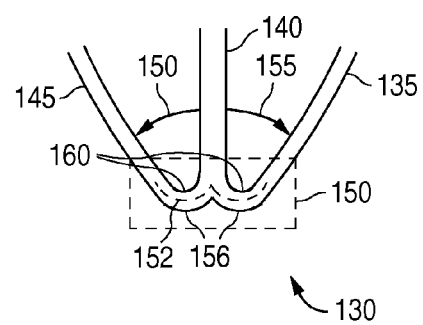

FIG. 4A depicts a partial planar side view of a portion 130 from a stent in an unexpanded state that includes curved section 150, straight sections 135, 140, and 145. Straight sections 135 and 140 are at an angle 155 and straight sections 140 and 145 are at an angle 151. As shown in FIG. 4B, radial expansion of the stent increases angles 150 and 155. The stress and strain in straight sections 135, 140, and 145 is relatively small. Section 150 experiences relatively high tensile stress and strain at concave portions 160 and relatively high compressive stress and strain at convex portions 156. A neutral axis 152 is a surface of zero strain that is the boundary between portions 156 and portions 160. The description and analysis relating to nonuniformity of stress and strain in an implantable medical device is not limited to the structures in FIGS. 2A-C, 3A-B, and 4A-B. Analysis of strain distribution in a device, or generally any structure, subjected to applied stress may be performed for a device or structure of virtually any geometry.

Figure 5:
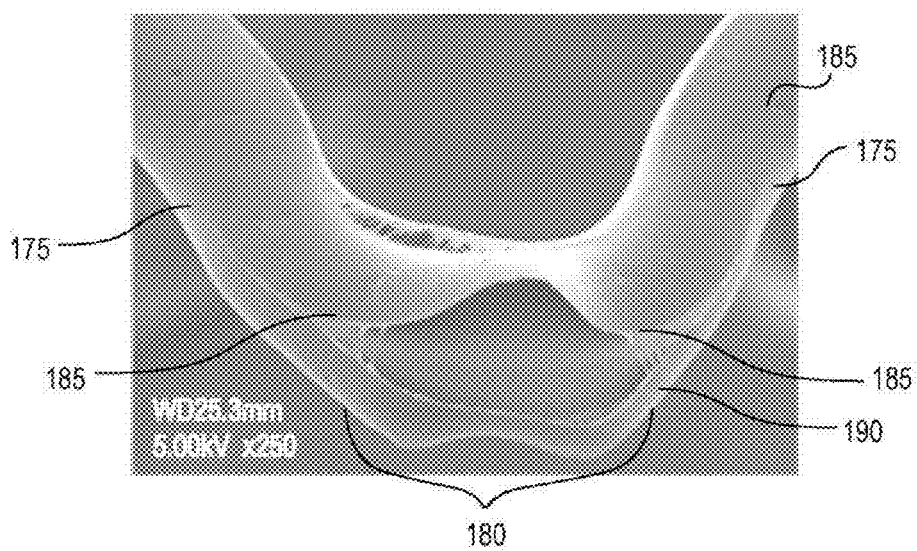
FIGS. 5-7 depict scanning electron microscope images of coating failure on the surface of stents.
Figure 6:
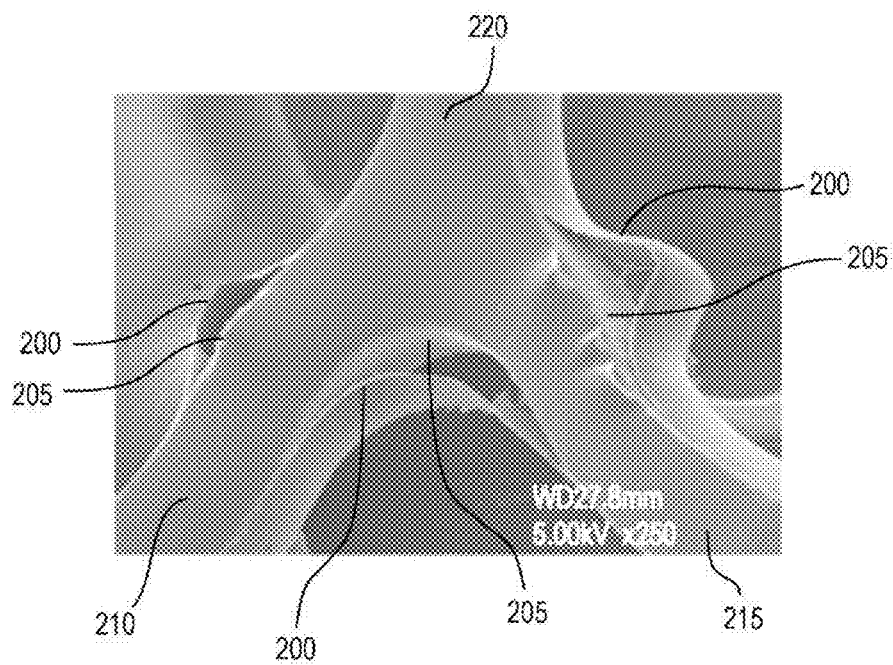
Figure 7:
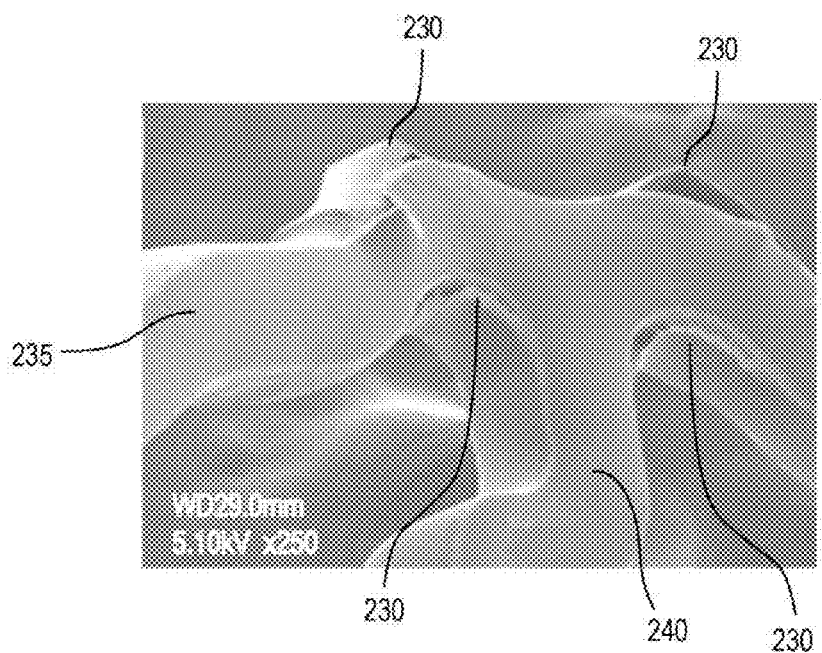

FIGS. 5-7 depict scanning electron microscope images of coating failure on the surface of stents. FIG. 5 depicts an image of a portion of a stent similar to the portion shown in FIGS. 2A and 2B. The image in FIG. 5 shows straight portions 175 and a curved portion 180. A coating 185 on portion 170 is torn and detached from a substrate 190 at curved portion 180. Coating 185 on straight portions 175 appears to have remained intact. FIG. 6 depicts an image of a portion of a stent similar to the portion shown in FIGS. 3A and 3B. The image in FIG. 6 shows that a coating 200 has torn and detached from a substrate 205 from the curved portions of the stent. Detachment has occurred primarily from the faces of the strut between the luminal and abluminal faces of the strut. As discussed above, the abluminal and/or luminal faces of the strut may have regions of relatively low strain proximate to a neutral axis. Coating 200 has remained intact on straight portions 210, 215, and 220. FIG. 7 depicts an image of a portion of a stent similar to the portion shown in FIGS. 4A and 4B. The image in FIG. 7 shows that a coating 230 has torn and detached from the substrate of the stent at or near the curved portions of the stent. As in FIG. 6, detachment has occurred primarily from the faces of the strut between the luminal and abluminal faces of the strut. As in FIG. 6, abluminal and/or luminal faces of the strut may have regions of relatively low strain proximate to a neutral axis. FIG. 7 shows that the coating has remained intact on straight portions 235 and 240.

Embodiments of the devices disclosed herein address the problem of tearing, delamination, peeling, and fracture of polymer-based coatings on implantable medical devices. In some embodiments, the problem may be addressed by selectively coating an implantable medical device in a manner that reduces the overall strain experienced by a coating during use of the device. Certain embodiments of a method of selectively coating an implantable medical device may include forming a nonuniform coating on an implantable medical device. The device may include a first section that has higher strain than a second section when the device is placed under an applied stress during use. Use of the device is intended to encompass both reduction of diameter of the stent, such as during crimping on a balloon, as well as radial expansion of the device. A strain on the nonuniform coating may be less than a strain on a uniform coating when the device is placed under the applied stress during use. A uniform coating refers to a coating that is the opposite of all of the characteristics of a nonuniform coating. In particular, a uniform coating is defined as: (1) no coating free portions of the device; (2) use of the same materials (e.g., polymers) or combination of materials; (3) coating having the same drug content and the same amount of drug at all portions of the device; (4) coating having the same type of drug at all portions of the device; (5) coating having the same thickness at all portions of the device; (6) coating material (e.g., polymer) having the same characteristics (such as elasticity) at all areas of the device; (7) use of the same coating additives or plasticizers at all portions of the device, and (8) the same quantity of coating material at all areas of the device.

As indicated above, the applied stress may be due to radial expansion of a device that is a radially expandable stent. In some embodiments, the first section may include at least a part of a curved and/or bent portion of at least one strut. The second section may include at least a part of a straight or substantially straight portion of at least one strut.

Several embodiments of the device and the method may include various nonuniform coatings and methods of forming nonuniform coatings that experience less strain than a uniform coating on a device when the device is placed under an applied stress during use. In one embodiment, the nonuniform coating may include coating or coating free portions of the first section of the device. In other embodiments, a nonuniform coating may include the use of materials (e.g., polymers) or combination of materials on a first section different from a second section of a device. Additionally, a nonuniform coating may have no drug content in a first section or an amount of drug at a first section different from a second section of the device. For example, the first section may have lower drug content than the second section, resulting in a more elastic coating in the first section than the second section. Furthermore, a nonuniform coating may have different types of drug at a first section than a second section of the device. For instance, the first section may have a type of drug in the first section that results in a more elastic coating in the first section than the second section. Other embodiments of a nonuniform coating may have a different thickness at a first section than a second section of the device. A thinner coating on the first section may be less subject to tearing, delamination, peeling, or fracture. In addition, a nonuniform coating may have coating material (e.g., polymer) that has different characteristics (such as elasticity) at a first section than a second section of the device. Furthermore, a nonuniform coating may include the use of different coating additives or plasticizers at a first section of the device. Another embodiment of a nonuniform coating may include a different quantity of coating material at a first section and a second section of the device. An additional embodiment of a nonuniform coating may include coating the first section and the second section with coating material and then removing at least a portion of the coating material applied to the first section.

Figure 8A:
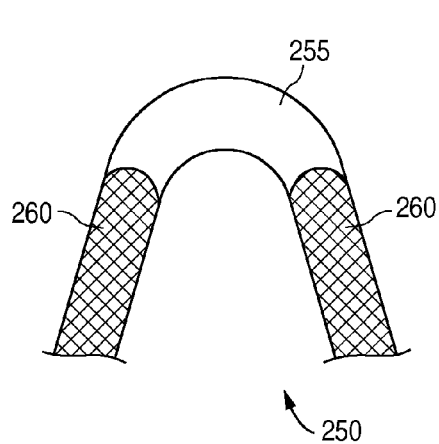
Figure 8B:
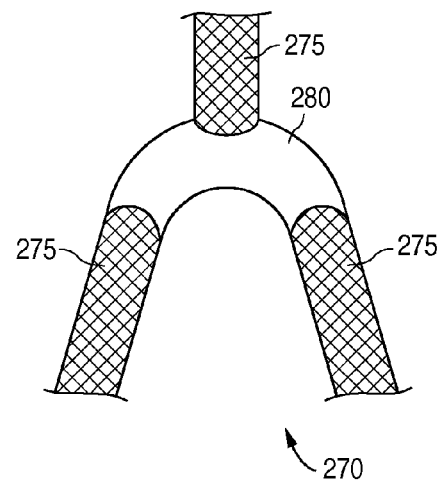
Figure 8C:
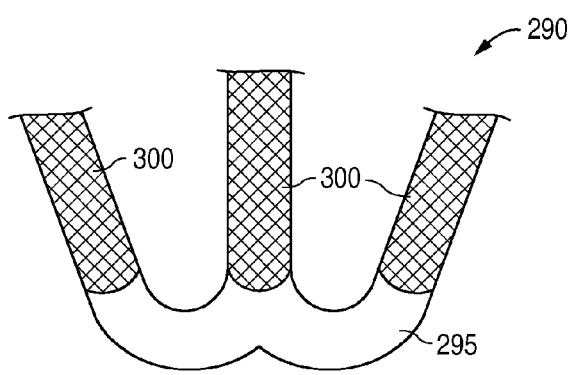

For example, FIGS. 8A-C depicts partial planar side views of portions of struts from a stent that are selectively coated. FIGS. 8A, 8B, and 8C are similar to portions depicted in 2A-C, 3A-B, and 4A-B, respectively. FIG. 8A depicts portion 250 with coated sections 260 and uncoated section 255. FIG. 8B depicts portion 270 with coated sections 275 and uncoated section 280. FIG. 8C depicts portion 290 with coated sections 300 and uncoated section 295. The uncoated sections in FIGS. 8A-C are sections that experience relatively high strain when a stent is under an applied stress during use. The coated sections experience relatively low or no strain in an expanded stent. In general, a reduced strain coating may be formed by coating a smaller fraction of a surface area of the first section than a fraction of a surface area of the second section. Additionally, certain embodiments of a nonuniform coating may include a thicker coating on at least a portion of the second section than on at least a portion of the first section of the device. Other embodiments of a nonuniform coating may include a coating on at least a portion of the first section having a different composition from a coating on at least a portion of the second section. In one embodiment, the coating on the first section may be more resistant to strain than a coating on the second section.

Further embodiments of a nonuniform coating with lower strain than a uniform coating may include a coating on parts of the first section that have relatively low strain. Some embodiments may include a coating on at least a portion of the first section at and/or proximate to a neutral axis of the device. For example, the coating may include a strip of coating material at and/or proximate to the neutral axis. As indicated above, along a neutral axis, the strain is zero. However, the strain increases dramatically moving away from the neutral axis. Several examples of neutral axes on portions of struts from stents are shown in FIGS. 2C, 3B, and 4B. In one embodiment, a nonuniform coating may include coating material on a portion of a first section at and/or proximate to a latitudinal midpoint of a luminal and/or abluminal surface of the first section. For a section of a strut that is symmetric along its longitudinal and latitudinal axis, the neutral axis runs along the latitudinal midpoint of a section. For example, FIG. 9A depicts a portion 310 with an uncoated section 315, coated sections 320, and a coated section 325. Coated section 325 is a strip of coating material at and proximate to the latitudinal midpoint of portion 310 which corresponds to a neutral axis of portion 310. Another example, is shown in FIG. 9B which depicts a portion 326 with an uncoated section 327, coated sections 328, and a coated section 329. Coated section 329 is a strip of coating material at and proximate to the latitudinal midpoint of portion 326 which corresponds to a neutral axis of portion 326.

Additional embodiments of a nonuniform coating with lower strain than a uniform coating may include a dot-like region of the coating material on a portion of the first section. In some embodiments, the portion of the first section may be at and/or proximate to a neutral axis of the device. As indicated above, the neutral axis may be at and/or proximate to a center or midpoint of a latitudinal width of a luminal and/or abluminal surface (see FIG. 1B) of the first section. For example, FIG. 10 illustrates a portion 330 with an uncoated section 335, coated sections 340, and coated sections 345. Portion 330 has neutral axis 350. Coated sections 345 are dot-like regions of coating material at and proximate to the latitudinal midpoint of portion 330. A desired radius of the dot-like region may depend on the elasticity and the adhesion properties of the coating. In some embodiments, a radius of the dot-like region may be greater than about one eighth and less than about three fourths, or more narrowly greater than about one fourth and less than about one half of a latitudinal width of the first section.

Additional embodiments of a nonuniform coating with lower strain than a uniform coating may include a band of coating material partially or completely around a latitudinal perimeter of the first section. The lateral band of coating material may act to dissipate the strain experienced by the implantable medical device. In addition, the lateral band may be disposed partially or completely around a lateral perimeter of the first section. For example, the band may be around a latitudinal perimeter of strut. In certain embodiments, a width of the band may be less than or equal to a latitudinal width (see FIG. 1B) of the first section. In other embodiments, a width of the band may be greater than or equal to one fourth and less than or equal to three fourths of a latitudinal width of the first section. In another embodiment, a width of the band may be about one third of a latitudinal width of the first section.

Figure 11A:
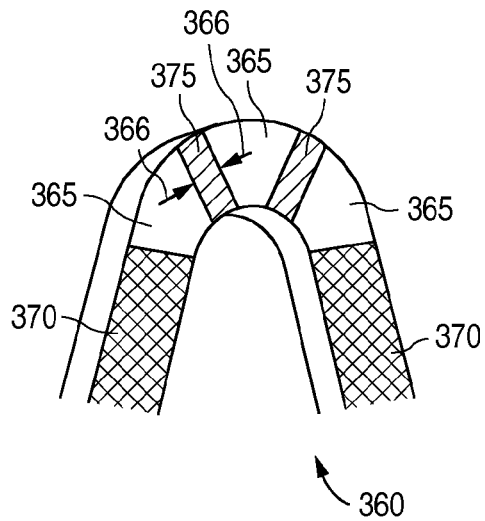
Figure 11B:
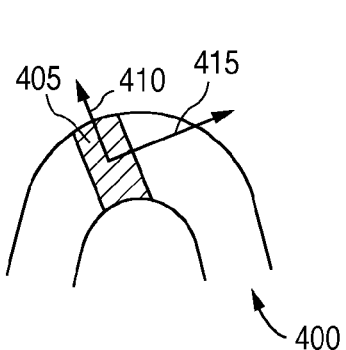
Figure 11C:
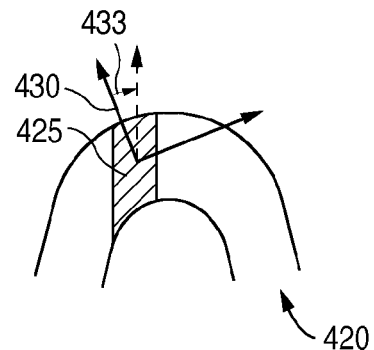

FIG. 11A depicts a portion 360 with uncoated sections 365, coated sections 370, and coated sections 375. Coated sections 375 are bands of coating material with a width 366 disposed partially around a latitudinal perimeter of portion 360. In some embodiments, the lateral band of coating material may run parallel or substantially parallel to the latitudinal axis of the first section. In other embodiments, the band of coating material may run at an angle greater than 0° and less than 90° to the latitudinal axis of the first section. In this case, the coating material may be a spiral band around a first section of the device with an axis of symmetry along the longitudinal axis. FIG. 11B depicts a portion 400 of a curved section of a strut with a band 405 of coating material. Band 405 runs parallel to a latitudinal axis 410 and perpendicular to a longitudinal axis 415. FIG. 11C depicts a portion 420 of a curved section of a strut with a band 425 of coating material that runs at an angle 433 relative to a longitudinal axis 430.

Figure 12:
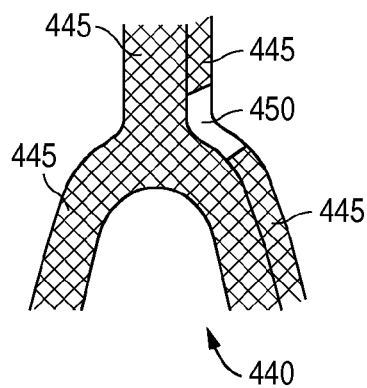

Another embodiment may include no coating or coating free portions on side-walls of curved or bent portions of struts. As shown in FIGS. 5, 6, and 7, peeling, tearing, delamination may tend to occur principally on the side-walls of curved or bent portions of struts. For example, FIG. 12 illustrates an embodiment of a portion 440 of a curved portion of a strut. Portion 440 has coated sections 445 and an uncoated side-wall portion 450.

Further embodiments of the methods and devices of addressing the problem of tearing and fracture of polymer-based coatings may include coating higher strain portions of a device with a different coating material than a lower strain area. In general, a flexible, low modulus coating with high elasticity may be more resistant to strain, and hence, less susceptible to failure than a stiff coating. A coating material may be modified to increase its resistance to strain by using components including, but not limited to, plasticizers and primers and mixtures of polymers. However, it may be desirable to limit the use of different or modified coating material to higher strain portions of the device to limit exposure of such additional components to a body.

Certain embodiments of a method of selectively coating an implantable medical device may include forming a coating of a first coating material on a first section of an implantable medical device and forming a coating of a second coating material on the second section of the device. The first section has higher strain than a second section when the device is placed under an applied stress during use. In some embodiments, the coating on the first section has greater resistance to strain than the coating on the second section. The phrase "greater resistance to strain" may refer to, but is not limited to, a greater elasticity, a lower tensile modulus, a lower compressive modulus, higher tensile strength, higher compressive strength, and/or better adhesion properties. A coating with a greater resistance to strain may be more resistant to mechanical failure such as fracture or separation from an underlying substrate.

In certain embodiments, the first coating material may include a polymer or a combination of polymers that have greater resistance to strain than a polymer in a second coating material. The polymers can be in blend, mix, conjugated, linked, entangled, or bonded form. Certain embodiments may include a coating on the first section with polymers that are more elastic that polymers in the coating on the second section. For example, the polymers on the first section may have a $T_g$ below human body temperature and the polymers on the second section may have a $T_g$ that is above human body temperature.

Additionally, in some embodiments, the resistance to strain of a polymer of the first coating material may be increased by including a plasticizer in the polymer. In general, a "plasticizer" is a chemical additive that increases the elasticity of a polymer. A plasticizer, which is usually a low molecular weight nonvolatile molecule, can be dissolved with the polymer before the applying a coating material to a device. An active agent may also act as a plasticizer.

It is desirable for a plasticizer for use in a coating of an implantable medical device to be biocompatible and nonvolatile or substantially nonvolatile. Low volatility is important since diffusion of a plasticizer through a vapor phase into other phases or components proximate to an implantable device may influence the effectiveness and safety of the device.

In addition, it is not desirable for a plasticizer to substantially or significantly affect the drug release kinetics or drug stability of active agents in a coating. However, it may be advantageous for a plasticizer to change the degradation rate of a biodegradable polymer in a polymer coating.

In one embodiment, a plasticizer can include low molecular weight oligomers of monomers forming a biodegradable polymer. For example, the oligomer can be a dimer, trimer, tetramer or oligomer of lactic acid, which forms PDLL or poly(D,L-lactic acid) (PDLLA). Some exemplary low molecular weight plasticizers may include cyclic or linear oligomers of glycolic acid, lactic acid, 3-hydroxypropanoic acid, 3-hydroxybutyric acid, 4-hydroxybutyric acid, 3-hydroxyvalerate, 4-hydroxyvalerate, 5-hydroxyvalerate, 3-hydroxyhexanoate, 4-hydroxyhexanoate, and 5-hydroxyhexanoate. Other exemplary plasticizers may include dimers or trimers of lactic acid. Lactic acid can be racemic or enantiomeric in D or L form. In one embodiment, the plasticizer is an oligomer of poly(D,L-lactic acid) (PDLLA) having a molecular weight in the range from 1000 Daltons to 5,000 Daltons. The low molecular weight oligomers can be formed by methods documented in the art (see, for example, see, for example, Michael Smith, Organic Synthesis, $2^{nd}$ Edition, McGraw-Hill, 2001).

In another embodiment, the plasticizer can be a fatty acid. The fatty acid can be synthetic or naturally occurring fatty acids. The fatty acid can be liquid or solid. Representative natural fatty acids include, but are not limited to, palmitoleic acid, lauric acid, oleic acid, linoleic acid, and arachidonic acid. Representative synthetic fatty acids include, for example, C6-C15 alkanoic acids such as heanoic acid, heptanoic acid, or octanoic acid. Additionally, plasticizers may also include esters of the fatty acids. It is believed that fatty acid esters do not influence the polymer degradation kinetics of the coating polymer or stability of the drug in a drug-delivery coating. Representative ester plasticizers may include the ethyl, propyl, and butyl ester of oleic acid. In addition, plasticizers may be a glyceride, such as a mono, di and triglyceride. The glycerides can be natural glycerides or synthetic glycerides and can contain any of the fatty acids described above. For example, most naturally occurring triglycerides contain stearate, palmitate, linoleic, oleic fatty facid, or a mixtures thereof. Further representative plasticizers may include synthetic or naturally occurring fatty alcohols including, but not limited to, fatty alcohols described in the FDA GRAS (generally recognized as safe) list. Additional representative examples of plasticizers may include citric acid esters for poly(L-lactide), lactide or lactic acid monomer such as ethyl lactate, a polyalkylene glycol such as polyethylene glycol (PEG), or a polyalkylene oxide.

Additionally, the resistance to strain of a coating on a first section of a device may be increased by enhancing the adhesion properties of the coating. In some embodiments, the resistance to strain of the coating on the first section may be increased by including at least one primer layer on the first section. In general, a "primer layer" is a coating layer on a surface that improves the adhesion of subsequent coating layers on the surface. In some embodiments, the primer layer may include one or more polymers.

As noted above, the presence of an active agent in a polymeric matrix can interfere with the ability of the matrix to adhere effectively to the surface of the device. Increasing the quantity of the active agent reduces the effectiveness of the adhesion. High drug loadings in the coating can hinder the retention of the coating on the surface of the device. A primer layer can serve as a functionally useful intermediary layer between the surface of the device and an active agent-containing or reservoir coating, or between multiple layers of reservoir coatings. The reservoir layer may include one or more active agents dispersed within one or more polymers. The primer layer provides an adhesive tie between the reservoir coating and the device—which, in effect, would also allow for the quantity of the active agent in the reservoir coating to be increased without compromising the ability of the reservoir coating to be effectively contained on the device during delivery and, if applicable, expansion of the device.

Figure 13A:
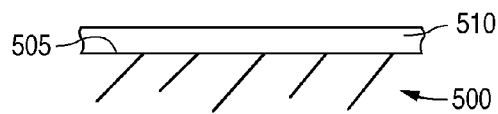
FIGS. 13A-13D illustrate coatings deposited over a surface of an implantable medical device.

Some of the embodiments of polymer coatings are illustrated by FIGS. 13A-D. The figures have not been drawn to scale, and the thickness of the various layers have been over or under emphasized for illustrative purposes. FIG. 13A depicts a first section of an implantable medical device 500, such as a stent, having a surface 505. A primer layer 510 is deposited on surface 505. The polymer in primer layer 510 may be a homopolymer, copolymer, terpolymer, etc. The polymer may also include random, alternating, block, cross-linked, blends, and graft variations thereof. For instance, primer layer 510 may include a poly(lactic acid).

Figure 13B:
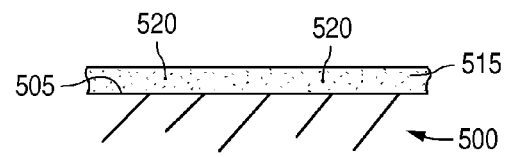

FIG. 13B depicts a reservoir layer 515 deposited on surface 505. The reservoir layer has a polymer and an active agent 520 dispersed in the polymer. The active agent may be, for example, 40-O-(2-hydroxy)ethyl-rapamycin, known by the trade name of EVEROLIMUS, available from Novartis as Certican™ Reservoir layer 515 may release the active agent when implantable medical device 500 is inserted into a biological lumen. Without a primer layer between surface 505 and reservoir layer 515, reservoir layer 515 may be more susceptible to failure as device 500 is implanted in a patient for treatment.

Figure 13C:
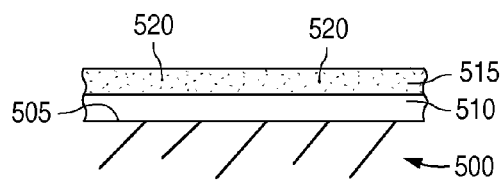

FIG. 13C depicts reservoir layer 515 deposited on primer layer 510. Primer layer 510 serves as an intermediary layer for increasing the adhesion between reservoir layer 515 and surface 505. Increasing the amount of active agent 520 admixed within the polymer can diminish the adhesiveness of reservoir layer 515 to surface 505. Accordingly, using an active agent-free polymer as an intermediary primer layer 510 allows for a higher active agent content for reservoir layer 515.

Figure 13D:
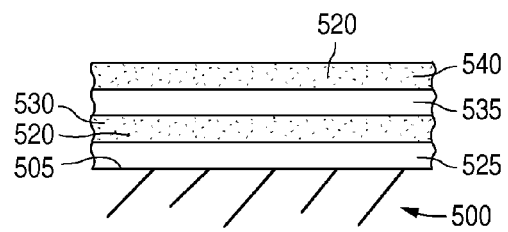

The coating may also have multiple primer and reservoir layers with the layers alternating between the two types of layers through the thickness of the coating. For instance, FIG. 13D depicts medical substrate 500 with a primer layer 525 deposited on surface 505, followed by reservoir layer 530 deposited on primer layer 525. A second primer layer, primer layer 535, can then be deposited on reservoir layer 530. Reservoir layer 540 is deposited over primer layer 535. Reservoir layers 530 and 540 have active agent 520 dispersed within the polymer. The different layers through the thickness of the coating can contain the same or different components. For instance, primer layers 525 and 535 can contain the same or different polymers. Furthermore, reservoir layers 530 and 540 can contain the same or different polymers or active agents.

By way of example, and not limitation, primer layer 510 in FIG. 13C can have any suitable thickness, examples of which can be in the range of about 0.1 to about 10 microns, more narrowly about 0.1 to about 2 microns. Reservoir layer 515 in FIG. 13C can have a thickness of about 0.1 microns to about 10 microns, more narrowly about 0.5 microns to about 2 microns. The amount of the active agent to be included on implantable medical device 500 can be further increased by applying a plurality of reservoir layers 515 on top of one another.

The primer layer can be formed by applying a polymer or prepolymer to the stent by conventional methods. For example, a polymer or a prepolymer can be applied directly onto the stent substrate in the form of a powder or by vapor deposition. In one embodiment, an unsaturated prepolymer (e.g., an unsaturated polyester or acrylates) is applied to the device, and then heat treated to cause the prepolymer to crosslink.

The polymer or prepolymer can also be applied by depositing a polymer composition onto the stent. The polymer composition can be prepared by combining a predetermined amount of a polymer or a prepolymer and a predetermined amount of a solvent or a combination of solvents. The mixture can be prepared in ambient pressure and under anhydrous atmosphere. If necessary, a free radical or UV initiator can be added to the composition for initiating the curing or cross-linking of a prepolymer. Heating and stirring and/or mixing can be employed to effect dissolution of the polymer into the solvent. The composition can then be applied by conventional methods such as by spraying the stent substrate with the composition.

The polymers used for the primer material should have a high capacity of adherence to the surface of an implantable device, such as a metallic surface of a stent, or a high capacity of adherence to a polymeric surface such as the surface of a stent made of polymer, or a previously applied layer of polymeric material.

Various methods may be used to form coatings as described herein. For example, a controlled deposition system can be used that applies various substances only to certain targeted portions of an implantable medical device. A representative example of such a system, and a method of using the same, is described in U.S. Pat. No. 6,395,326 to Castro et al. A controlled deposition system can be capable of depositing a substance on an implantable medical device having a complex geometry, and otherwise apply the substance so that coating is limited to particular portions of the device. The system can have a dispenser and a holder that supports the medical substrate. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir which holds a composition prior to delivery, and a nozzle having an orifice through which the composition is delivered. One exemplary type of dispenser assembly can be an assembly that includes an ink-jet-type printhead. Another exemplary type of a dispenser assembly can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

The substances of the present invention can also be selectively deposited by an electrostatic deposition process. Such a process can produce an electrically charged or ionized coating substance. The electric charge causes the coating substance to be differentially attracted to the device, thereby resulting in higher transfer efficiency. The electrically charged coating substance can be deposited onto selected regions of the device by causing different regions of the device to have different electrical potentials.

Furthermore, selective coating of an implantable medical device may be performed using photomasking techniques. Deposition and removal of a mask can be used to selectively coat surfaces of substrates. Masking deposition is known to one having ordinary skill in the art.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device comprising:
   a plurality of struts that form an abluminal surface, a luminal surface, and side-walls between the abluminal and luminal surfaces, the struts including strut straight sections and a strut curved section, at least two of the strut straight sections joined by the strut curved section; and
   a nonuniform coating disposed over the side-walls,
   wherein each side-wall has a side-wall portion at one or more of the strut straight sections, and the nonuniform coating is disposed over the side-wall portions at the strut straight sections, wherein each of the side-walls has a side-wall portion at the strut curved section, and no material of the nonuniform coating is disposed over at least one of the side-wall portions at the strut curved section, and the nonuniform coating is disposed over an entirety of the abluminal surface at the curved section.

2. The device of claim 1, wherein the nonuniform coating is disposed over the abluminal surface at the straight sections.

3. The device of claim 1, wherein the nonuniform coating is disposed over the luminal surface at the curved section.

4. The device of claim 1, wherein the nonuniform coating is disposed over the luminal surface at the straight sections.

5. The device of claim 1, wherein the struts are parts of a stent configured to be crimped onto a balloon.

6. The device of claim 1, wherein the struts are parts of a stent configured to expand or a self-expand.

7. A method of selectively coating an implantable medical device, the method comprising:
forming a nonuniform coating on a plurality of struts of the medical device, wherein
the struts form an abluminal surface, a luminal surface, and side-walls between the abluminal and luminal surfaces,
the struts include strut straight sections and a strut curved section,
at least two of the strut straight sections are joined by the strut curved section,
each side-wall includes a side-wall portion at one or more of the strut straight sections and a side-wall portion at the strut curved section, and
the forming of the nonuniform coating is performed such that the nonuniform coating (a) is disposed over the side-wall portions at the strut straight sections, (b) is not disposed over at least one side-wall portion at the strut curved section, and (c) is disposed over an entirety of the abluminal surface at the curved section.

8. The method of claim 7, wherein the forming of the nonuniform coating is performed such that the nonuniform coating is disposed over the abluminal surface at the straight sections.

9. The method of claim 7, wherein the forming of the nonuniform coating is performed such that the nonuniform coating is disposed over the luminal surface at the curved section.

10. The method of claim 7, wherein the forming of the nonuniform coating is performed such that the nonuniform coating is disposed over the luminal surface at the straight sections.

11. The method of claim 7, wherein the struts are parts of a stent configured to be crimped onto a balloon.

12. The method of claim 7, wherein the struts are parts of a stent configured to expand or a self-expand.

* * * * *